United States Patent [19]

Bjare et al.

[11] Patent Number: 4,990,258
[45] Date of Patent: Feb. 5, 1991

[54] MONITOR FOR THE CONTROL AND/OR CHECKING OF TWO OR MORE FUNCTIONS

[75] Inventors: Bjorn A. Bjare, Lund; Bengt-Ake G. Gummesson, Bara; Anders G. Eckerbom, Bromma; Jan P. Sternby, Lund, all of Sweden

[73] Assignee: Gambro AB, Sweden

[21] Appl. No.: 868,354

[22] Filed: May 29, 1986

[30] Foreign Application Priority Data

Jun. 4, 1985 [SE] Sweden .................. 8502756

[51] Int. Cl.$^5$ ............................................ B01D 61/34
[52] U.S. Cl. ........................................ 210/647; 210/90; 210/96; 210/321.65
[58] Field of Search ................. 210/321.2, 321.3, 141, 210/143, 85, 87, 90, 96.1, 647, 321.65; 364/415, 416, 417, 200

[56] References Cited

U.S. PATENT DOCUMENTS

| | | | |
|---|---|---|---|
| 3,947,665 | 3/1976 | Hundley | 364/162 X |
| 4,153,554 | 5/1979 | von der Heide et al. | |
| 4,180,854 | 12/1979 | Walden et al. | 364/200 |
| 4,370,983 | 1/1983 | Lichtenstein | 210/321.2 X |
| 4,514,798 | 4/1985 | Lesche et al. | |

FOREIGN PATENT DOCUMENTS

| | | |
|---|---|---|
| 3031966 | 4/1982 | Fed. Rep. of Germany . |
| 2489012 | 8/1981 | France . |
| 2057717 | 5/1980 | United Kingdom . |
| 2141838A | 8/1981 | United Kingdom . |

Primary Examiner—Frank Spear
Attorney, Agent, or Firm—Lerner, David, Littenberg, Krumholz & Mentlik

[57] ABSTRACT

A control panel for regulating plural parameters is provided with plural displays, each associated with one parameter. A single manually moveable knob is provided for entering a manually variable signal. Individual actuators such as push buttons are disposed adjacent each of the display means. The control panel is arranged to interpret the variable signal provided by the maneuvering element or knob as a new value for a control constant associated with a particular parameter depending upon which push button is actuated. The operator may select a particular parameter for resetting by pressing the button adjacent the display for that particular parameter. The panel simplifies setting of plural parameters in complex control systems such as the control system for a hemodialysis apparatus. The control system may incorporate plural microprocessors. Control data input into the microprocessors is digitally duplicated and transferred between the microprocessors to avoid entry of conflicting data into the two separate microprocessors.

20 Claims, 6 Drawing Sheets

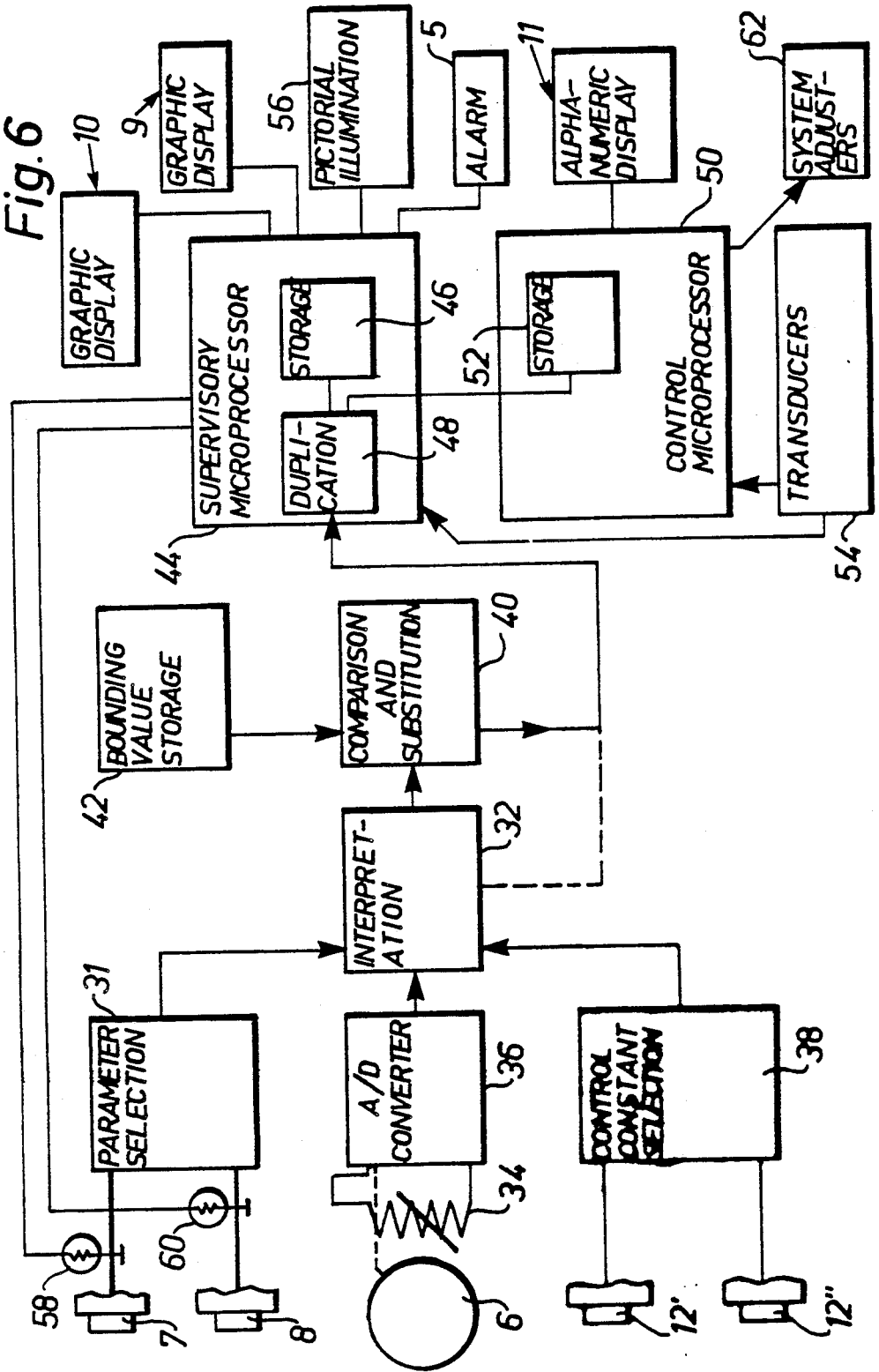

MONITOR FOR THE CONTROL AND/OR CHECKING OF TWO OR MORE FUNCTIONS

FIELD OF THE INVENTION

The present invention relates to automatic control systems, and more particularly to control panels for use therewith. Still more particularly, the present invention relates to control panels and control systems which are particularly suitable for the control cf complex equipment and processes such as hemodialysis or blood purification procedures utilized in patients with diminished or nil renal function.

BACKGROUND OF THE INVENTION

Equipment for hemodialysis has become widely available in recent years. Particularly suitable systems are described in U.S. Pat. Nos. 4,122,010; 4,158,034; 4,293,409; 4,194,974; 4,191,359; and 4,536,201, the disclosures of which are incorporated herein by reference thereto. Additional aspects of hemodialysis equipment and methods are also described in British Pat. No. 2,003,274, and in co-pending commonly assigned U.S. patent application Ser. No. 531,277, the disclosures of which are also incorporated herein by reference thereto.

Although the hemodialysis equipment and methods disclosed in the aforementioned patents and applications provide effective treatment modalities, there has been a need for still further improvement. There have been particularly acute needs for improvements in the control panels or interfaces between the machine operator and the machine. Hemodialysis processes typically entail the control of numerous operating parameters, such as, e.g., various fluid temperatures, ultrafiltration rates, ultrafiltrate volumes, transmembrane pressures or pressure differentials across the dialysis membrane itself, and various different fluid flows. The control of blood flow to and from the machine, venous pressure, arterial pressure and blood temperature may also be required. Each of these parameters may be regulated according to one or more control constants. In the simplest form of said regulation, the system may merely monitor deviations of the actual value of the parameter in question from a set point or desired value and undertake corrective action. Typically, however, upper and lower limits are also provided for some or all of these parameters as an additional safety factor. Thus, the system may then monitor the actual value of the parameter in question and generate an alarm signal, where the actual value is outside the range between the upper and lower alarm limits Accordingly, three different values of the three different control constants—lower limit, set point and upper limit—must be supplied to the control system for each parameter where this scheme is employed.

The machine operator must therefore enter a large number of different values or different control constants into a system to set the system for desired modes of operation. In apparatus of this nature which has been utilized heretofore, the control panel typically has incorporated a separate, continuously movable maneuvering element such as a control knob or slide for each different control constant to be entered. Arrangements of this nature require a great number cf knobs and the like on the control panel, and hence make the control panel confusing and difficult to use. The operator may encounter difficulties in determining which knob or maneuvering element should be adjusted to alter a given function of the system. These difficulties are compounded where the knobs or other control elements are dispersed on the panel, so that a given knob may be remote from the gauge or indicator for the parameter associated with that knob. Such confusion can be inconvenient for the operator and can also present a safety hazard if the wrong control constant is adjusted by mistake.

Moreover, a further safety hazard can be created if the operator enters the wrong value for a control constant. The operator may mistakenly set a value for an upper alarm limit on a parameter which is orders of magnitude too high, and hence may effectively disable the alarm function of the system. Manifestly, such an error can create a safety hazard, inasmuch as the alarm would not operate even though a potentially dangerous condition exists.

Where the system incorporates digital microprocessors for comparing the actual values of the various parameters with the associated control constants and initiating appropriate control or alarm action, it is most desirable to use at least two microprocessors including a supervisory microprocessor and a control microprocessor, each microprocessor having a storage register associated therewith. The control constants are stored in the registers associated with each of the microprocessors. The control microprocessor may adjust operation of the system based on a comparison of actual measured values for the various parameters with the appropriate set input value, whereas the supervisory microprocessor compares the actual measured values with the upper and lower limit values and generates an alarm if any parameter varies beyond the essential upper or lower limit. The two microprocessors provide redundancy and hence increased safety.

There has been a problem heretofore in the operation of redundant microprocessor systems of this nature, where such systems are associated with a control panel having analog devices such as knobs or other movable maneuvering elements for setting the values of the control constants. Typically, the maneuvering elements are associated with analog electrical devices such as potentiometers, so that the setting of each knob or other maneuvering element must be interpreted and converted into a digital value of the associated control constant by devices such as analog-to-digital converters. Such analog devices and converters typically suffer from certain inaccuracies. These inaccuracies may result in the storage of different values for various control constants in the storage registers associated with the two microprocessors. For example, the set point values supplied to the storage register associated with the control microprocessor by the analog-to-digital converter may be above the upper limit value supplied to the storage register associated with the supervisory microprocessor even though the operator has attempted to select a set point value between the upper and lower limit values. If such a mismatch occurs, adjustment of the system by the control microprocessor will cause the actual value of the operating parameter to rise above the upper limit applied by the supervisory microprocessor, which in turn will cause the supervisory microprocessor to continually signal an alarm condition.

SUMMARY OF THE INVENTION

In accordance with the present invention, solutions to these problems have now been provided by applicant's discovery of a control panel, which according to one aspect of the present invention incorporates manually controllable input means for setting manually selected new values of the control constants and supplying these manually adjustable values of the control constants to the system. The control panel also includes comparison and substitution means for comparing the manually selected new value supplied by the manually controllable input means for each critical constant with a preset, invariant range defined by upper and lower bounding values for the critical constant in question. The control and substitution means supplies to the system a new value for the critical constant within the preset invariant range in place of the manually selected value if the manually selected value is outside of the preset invariant range. The present invariant range applied by the comparison means for each critical constant is selected to encompass a range of values which provides safe operation of the system. Thus, if the operator, through error, attempts to enter a value for a critical control constant which could result in unsafe operation of the system, the comparison and substitution means will override his erroneous selection and will provide a safe value to the system. In a preferred embodiment, the substitution means is operative to supply the lower bounding value of the preset range to the system when the manually selected value is less than the lower bounding value and to supply the upper bounding value to the system when the manually selected value of the critical constant is greater than the upper bounding value.

According to another aspect of the present invention, the control panel is provided with a plurality of separate display means, preferably graphic display means, one of the display means being associated with each of the parameters to be controlled. Each of the display means is operative to display the value of one or more control constants employed by the system for the associated parameter. Preferably, each display means is also operative to display the actual measured value of the associated parameter during operation of the system. The control panel also includes variable signal means including a single manually movable maneuvering element for providing a manually variable signal dependent upon the position of the maneuvering element. The control panel also incorporates parameter selection means which includes a plurality of manually operable actuators, such as push buttons or touch pads, one of the actuators being disposed at a portion on the control panel preferably adjacent each of the display means. The parameter selection means is operative to select the parameter associated with one of the display means upon manual operation of the actuator associated with or adjacent to such display means. The panel also includes interpretation means for interpreting the signal provided by the variable signal means as a new value of a control constant for the parameter selected by the parameter selection means and supplying the new value of the control constant to the system. For example, where the parameters controlled by the system include transmembrane pressure and ultrafiltrate volume, the control panel may incorporate one display associated with transmembrane pressure, an actuator button adjacent that display, another graphic display associated with ultrafiltrate volume and an actuator button adjacent that display, and may also incorporate a single maneuvering element in the form of a knob. To adjust the value of a control constant such as a set point applied by the system with respect to transmembrane pressure, the operator simply actuates the actuator or button adjacent to the transmembrane pressure display and adjusts the maneuvering element as desired. To adjust the set point for ultrafiltrate volume, the operator instead now actuates the button adjacent the ultrafiltrate volume display, but the adjustment of the single maneuvering element or knob is substantially the same.

Where the system applies several control constants with respect to each parameter, such as a set point, an upper limit, and a lower limit, each of the displays is preferably arranged to display all of these control constants as well as the actual measured operating value of the associated parameter. The control panel may further include manually operable control constant selector means for selecting a particular one of the plural control constants for the particular parameter selected by the actuator means. The control constant selector means may include default means for automatically selecting set point as the particular control constant to be adjusted, and selecting upper limit or lower limit for adjustment only upon manual actuation of the selector means. Thus, the control constant selector means can include upper limit and lower limit actuators for manual actuation, and these may preferably be disposed adjacent the single maneuvering element or knob used to vary the control constant For example, where the system is arranged to apply an upper limit, a lower limit, and a set point in regulation of transmembrane pressure, the control panel may be arranged so that manual operation of the actuator button adjacent the transmembrane pressure display and operation of the manually adjustable knob or maneuvering element will vary the set point for transmembrane pressure, whereas the same operations in conjunction with deliberate depression of the upper limit selector button will adjust the upper limit for transmembrane pressure.

In accordance with another embodiment of the apparatus of the present invention, the control panel may include limit adjustment means automatically adjusting the upper and lower limit values for a particular parameter when the set point value for such parameter is manually changed.

Juxtaposition of the actuator associated with each parameter and the display associated with the same parameter facilitates easy and accurate selection of particular parameters and hence facilitates adjustment of the control constants associated with the various parameters of the system. Use of a single manually adjustable knob or maneuvering element significantly facilitates both the construction and the operation of the system. In a particularly preferred embodiment, for use with a system which incorporates a fluid flow path, the control panel may include a pictorial representation of the actual fluid flow path incorporated in the system. Typically, some or all of the parameters to be controlled by the system pertain to conditions prevailing at particular locations along the fluid flow path. In a particularly preferred embodiment, the control panel according to this aspect of the present invention may have some or all of the various displays and actuators disposed along the pictorial representation of the flow path in positions corresponding to the locations on the actual flow path to which the associated parameters pertain. Where the system includes plural flow paths, such as both a normal and a bypass path, the control panel may include pictorial representations of the plural flow paths, and may include means for selectively illuminating the pictorial representation representing the flow path actually in use.

The control panel according to this aspect of the present invention facilitates reading of the individual displays inasmuch as the operator can instantly select the appropriate display by scanning along the pictorial representation of the flow path to the point along the flow path associated with the parameter of interest. As the actuator which must be operated to set the control constants for each parameter is disposed adjacent the display for that parameter, the same scanning technique which leads the operator to the appropriate display also will lead him to the appropriate actuator. Thus, control panels according to this aspect of the invention further facilitate rapid, error-free setting of the control constants.

In accordance with another aspect of the present invention, a control system is provided with a plurality of microprocessors and a plurality of storage registers, the number of storage registers being at least equal, and preferably equal, to the number of microprocessors. One of the storage registers is associated with each of the microprocessors. Each of the microprocessors is arranged to control or monitor the same parameters in the controlled process, and each microprocessor is arranged to apply, in its monitoring and/or control operation, values of control constants stored in the associated storage register. Manually controllable input means are provided for supplying new values of the control constants to the system. Digital duplication means are provided for digitally duplicating the new values of the control constants supplied by the input means and entering the duplicated values into all of the storage registers. Because each new value is duplicated digitally rather than read separately from an analog element of the input means for entry into each storage register, identical values are entered into all of the registers. Thus, errors in the analog-to-digital conversion apparatus and other elements associated with the input means cannot result in storage of different values for the control constants in the storage registers associated with the various microprocessors.

Display means included in the apparatus preferably are arranged to display the new values entered into at least one of the storage registers. As the operator adjusts the value of each parameter, he naturally observes the display means to determine the value which he has set. Because the displayed value will be the value actually stored in the storage register, after introduction of any errors by the input means, the operator's natural action in observing the displayed values and continuing the adjustment until the desired value is displayed will automatically compensate for any errors introduced by the input means. Thus, errors caused by the input means will not result in storage of incompatible values for the different control constants, such as incompatible set points and limits. The digital duplication means may be arranged to copy the new values from the storage register associated with the supervisory microprocessor into the storage register associated with the control microprocessor. The display means may include separate displays to display the values of the control constants entered in both storage registers, so that any errors introduced by the digital duplication means can also be detected by observation of the displays.

These and other objects, features, and advantages of the present invention will be more readily apparent from the detailed description of the preferred embodiment set forth below, taken in conjunction with the accompanying drawings.

BRIEF DESCRIPTION OF THE DRAWINGS

FIG. 6 is a schematic functional diagram of the elements in a system incorporating the control panel of FIGS. 1-4.

DETAILED DESCRIPTION

Figure 1:
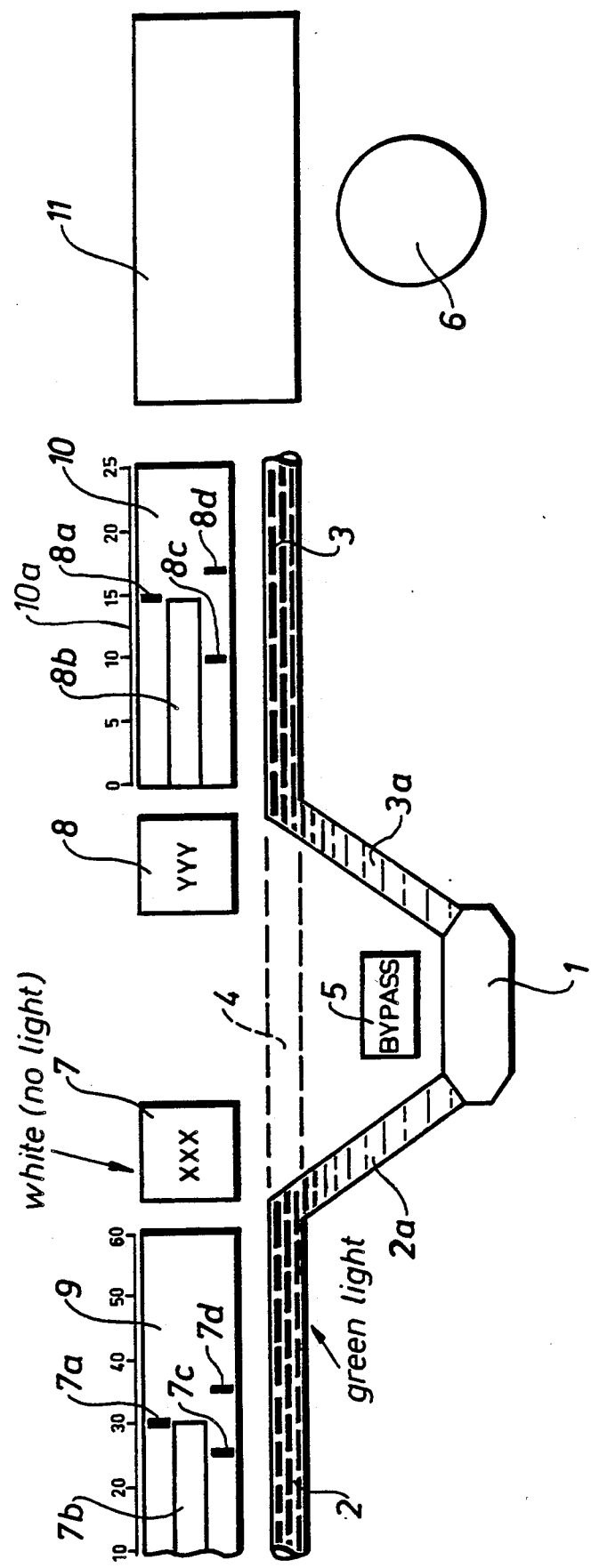
FIG. 1 is a schematic frontal view of a control panel for a system controlling two parameters or variables.

Referring to FIGS. 1-4 and 6 there is shown a control panel and system which is arranged for the control of two variables or parameters in a dialysis system which includes a dialyzer, a dialysis fluid inlet line, a dialysis fluid outlet line and a dialysis fluid bypass line for directly connecting the inlet line to the outlet line, and hence bypassing the dialyzer. The control panel, as illustrated in FIGS. 1-4, includes a pictorial representation of the actual fluid flow path in the system, and hence includes a pictorial element 1 representing the dialyzer, pictorial elements 2 and 2a representing the fluid inlet lines to the dialyzer, and pictorial elements 3 and 3a representing the fluid outlet lines. Also, a pictorial representation 4 depicts the bypass line. A bypass alarm signal light 5 is provided between the pictorial representation 4 of the bypass line and the pictorial representation 1 of the dialyzer itself. The single manually rotatable knob or maneuvering element 6 is disposed on the front surface of the panel. Two graphic displays 9 and 10 are also provided, with each such display being associated with one operating parameter of the system. Display 9 is thus associated with a parameter denominated "xxx", which pertains to the conditions prevailing at the inlet conduit 2, and graphic display 10 is associated with a parameter denominated "yyy," which pertains to the conditions prevailing at the outlet conduit 3. Graphic display 9 is disposed adjacent inlet conduit 2 and includes a common linear scale 9a with associated numerals. The display also includes illuminated indicia 7a, 7c and 7d, representing the values of control constants for par-meter xxx, in this case the set point represented by indicia 7a, the lower limit represented by indicia 7c, and the upper limit represented by indicia 7d. The positions of these indicia along scale 9a represent the values of these control constants. Graphic display 9 also includes a bar display 7b for displaying the actual measured value of parameter xxx. The length of bar 7b, and hence the position of the right hand edge of the bar along scale 9a represents the actual value of parameter xxx. A manually operable actuator or button 7, marked with the name of the parameter or "xxx", is disposed adjacent display 9.

In a similar fashion, the display 10 for parameter yyy, pertaining to the outlet conduit of the system, is disposed adjacent the pictorial representation 3 of the outlet conduit. Display 10 is generally similar to display 9, and includes a scale 10a, illuminated indicators 8a, 8c and 8d for displaying the set point, lower limit and upper limit for parameter yyy, and a bar graph 8b for indicating the actual value of parameter yyy. An actuator 8 is disposed adjacent display 10 and is labeled with the name of the associated parameter yyy. Also arranged on the front of the control panel are control constant selector buttons 12, which include an upper limit selector button 12' and a lower limit selector button 12", both disposed adjacent manually rotatable knob or maneuvering element 6. An alphanumeric display 11 is disposed on the panel face immediately above knob 6.

As illustrated in FIG. 6, actuators 7 and 8 are linked to parameter selection means 31, which in turn is connected to interpretation means 32. Maneuvering element knob 6 is linked to a potentiometer 34, which in turn is connected to an analog-to-digital converter 36. Converter 36 is also connected to interpretation apparatus 32. Control constant selector buttons 12' and 12" are linked to control constant selection means 38 which in is also linked to interpretation means 32. Interpretation means 32 is in turn connected to a comparison and substitution apparatus 40, which is linked to a bounding value storage register 42.

As explained below, these components provide new values of the control constants to the control system. The control system includes a supervisory microprocessor 44 incorporating a storage register 46 and duplication means 48. The control system also includes a control microprocessor 50 incorporating a further storage register 52. Both of the microprocessors are linked to transducers 54 arranged to measure the actual values of the various operating parameters of the actual system.

Supervisory microprocessor 44 is arranged to control graphic displays 9 and 10 and bypass alarm 5. The supervisory microprocessor is also arranged to control pictorial illumination unit 56 so as to selectively illuminate each segment of the pictorial representation 1, 2, 2a, 3, 3a and 4 with red light or with green light, as instructed by the supervisory microprocessor, or to leave each segment unilluminated. The supervisory microprocessor is also connected, via appropriate drivers (not shown) to illuminators 58 and 60 disposed physically within actuator buttons 7 and 8.

The control microprocessor 50 is linked to alphanumeric display 11, and is also to linked to the adjustable element 62 of the dialyzer and associated flow conduits. These adjustable elements typically include valves, variable electric resistance heaters, and the like.

Although parameter selection means 31, interpretation means 32, control constant selection means 38, analog-to-digital converter 36, bounding value storage means 42, and comparison and substitution means 40 are illustrated in FIGS. 6 as being separate from the microprocessors, it should be clearly understood that such depiction is solely for the sake of clarity of illustration. In actual practice, some or all of these elements can actually be incorporated in one or both of the microprocessors.

FIG. 1 illustrates the condition of the panel face during normal operation, without adjustment of any of the control constants. In this condition, illuminators 58 and 60 (FIG. 6) are inactive, so that actuator buttons 7 and 8 are not illuminated. Pictorial illumination means 36 (FIG. 6) illuminates the pictorial representations of the dialyzer 1, the inlet conduits 2 and 2a, and the outlet conduits 3 and 3a with green light, and leaves the pictorial representation 4 of the bypass conduit unilluminated. The bypass alarm light 5 is likewise unilluminated. Alphanumeric display 11 is blank, and graphic display 9 is actuated to display the values of set point, lower limit and upper limit for parameter xxx stored in the storage register 46 of the supervisory microprocessor 44, and also to display the actual value of parameter xxx as measured by the transducers 54. Likewise, graphic display 10 displays the set point, lower limit and upper limit for parameter yyy, also as stored in register 46, and also displays the actual value of parameter yyy. During normal operation, the actual value of each parameter is close to its set point and within the range defined by the upper and lower limits for this parameter. Inasmuch as the set point, actual value and limits for each parameter are clearly displayed along a common scale on a single graphic display, normal operation of the system is readily verifiable and the system condition as a whole can be readily determined by mere visual inspection of the panel.

Figure 2:
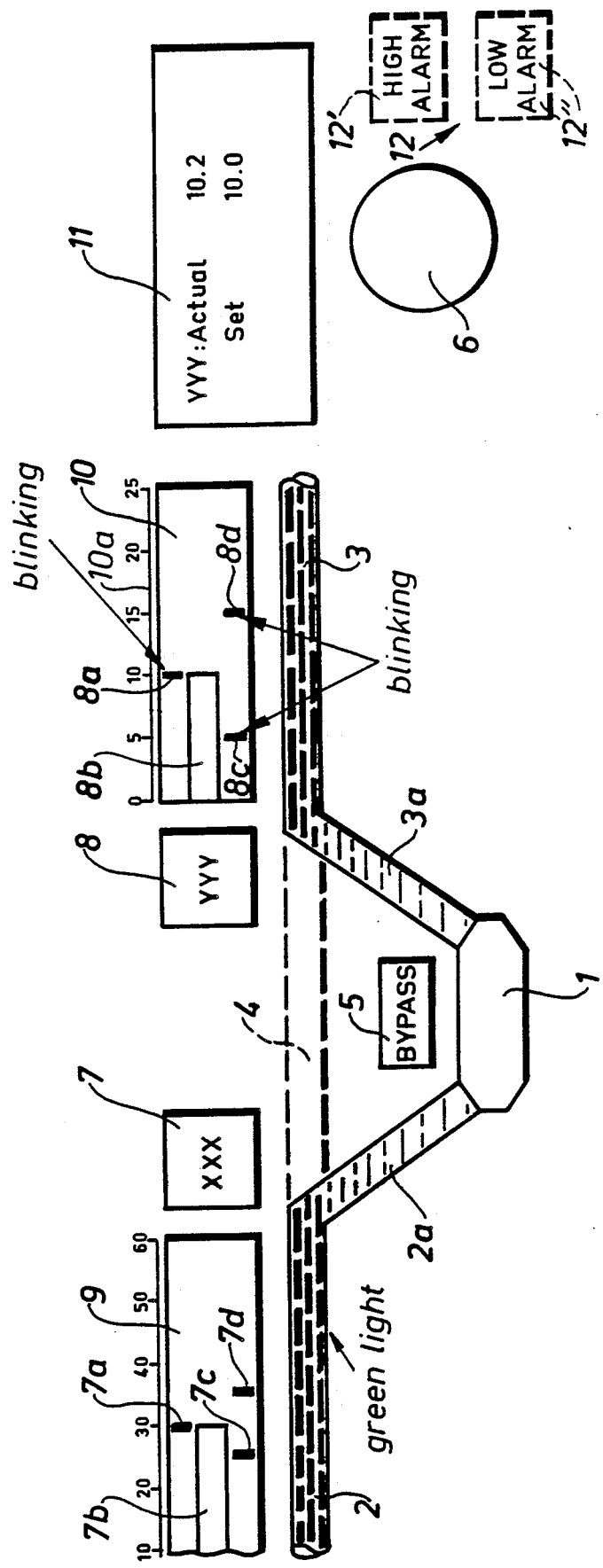
FIGS. 2-4 are views similar to FIG. 1, depicting the same panel in different operating states.

FIG. 2 illustrates the condition of the panel during adjustment by the operator of the set point for parameter yyy. Upon manual actuation by the operator of actuator or button 8 associated with parameter yyy, parameter selection means 31 selects parameter yyy. This selection is conveyed to supervisory microprocessor 44, which in turn instructs graphic display 10 to flash the illuminated indicia 8a, 8c and 8d, for the control constants associated with parameter yyy. In the condition illustrated, the operator has not depressed either upper limit selector button 12' or lower limit selector button 12". Accordingly, control constant selection means 38 selects the set point for parameter yyy, rather than the upper limit or lower limit for that parameter as the particular control constant to be adjusted, and signals interpretation means accordingly. The interpretation means thus interprets the manually variable signal generated by manual adjustment of maneuvering element or knob 6 and operation of analog-to-digital converter 36 as a new value for the set point for parameter yyy. The new value of parameter yyy is passed to comparison and substitution means 40. The comparison and substitution means compares the new value with preset, invariant upper and lower bounding values for the set point of parameter yyy stored in bounding value storage means 42. If the new value of the set point generated by interpretation means 32 is outside the range defined by these bounding values, then the comparison and substitution means 40 would substitute a value within such a range for the new value generated by the interpretation means. In the situation illustrated in FIG. 2, however, the new value generated by the interpretation means is within this range, so that the new value passes unaltered from the interpretation means to the supervisory microprocessor 44. The duplication means incorporated in the supervisory microprocessor digitally duplicates this value and enters the same value into both storage registers 46 and 52. In one arrangement, microprocessor 44 may be arranged so that the new values are entered into register 46 and then copied from that register by duplication means 48 into register 52. Control microprocessor 50 drives alphanumeric display 11 to show both the actual measured value of parameter yyy, as obtained from transducers 54, and also to show the value of the set point for this parameter last entered into register 52. Because the values of the set point are duplicated digitally, the exact same value will be stored in register 46 and in register 52. Moreover, because the value as stored in register 52 is fed back to the operator via alphanumeric display 11, as illustrated in FIG. 2, the operator will control his actuation of knob 6 according to the set point values as actually input into the storage registers. Accordingly, inaccuracies in 34 or analog-to-digital converter 36 are of little consequence. Such errors will not result either in the storage of divergent values in the two storage registers 46 and 52, or in the storage of incorrect values. Also, if the operator attempts to set an incorrect value such that the comparison and substitution means replaces the manually set value with one of the preset bounding means, the bounding limit rather than the manually set value will be displayed on display 11. Accordingly, the displayed value will not change as the operator adjusts the knob further in the wrong direction, thus warning the operator of his error. Additional indications of such an error can also be provided.

During the setting process, the supervisory microprocessor adjusts the position of the indicia 8a for the set point along the scale 10a of display 10, so as to reflect the new set point value. As the set point is thus adjusted, and thereafter, the control microprocessor 50 will compare the actual value of parameter yyy from the transducers from the new set point and will adjust the system adjuster components 62 to drive the actual value of this parameter towards the set point value.

When upper alarm limit selector button 12, is depressed, the control constant selection means 38 selects the upper limit control constant for adjustment. Thus, if the upper limit selection button 12' is actuated in conjunction with parameter selection button 8, the interpretation means will interpret these signals derived from manually adjustable maneuvering element or knob 8 via potentiometer 34 and converter 36 as a new value for the upper limit of parameter yyy. In that event, the comparison and substitution means will compare the new value with bounding values appropriate to the upper limit, rather than to the set point for parameter yyy and control microprocessor 50 will cause alphanumeric display 11 to display both the actual value of parameter yyy and the new upper limit value input into and stored in register 52. Likewise, with combined actuation of parameter selection button 8 and lower limit selection button 12", the variable signal derived from operation of knob 6 will be interpreted as a new value and for the lower limit of parameter yyy. As will be appreciated, the same action pertains to the setting of those parameters which requires actuation of button 7, rather than button 8. In each case, the signal derived from operation of knob 6 is interpreted as a new value for the particular control constant selected by the control constant selection means for the particular parameter selected by the parameter selection means. The identity of the parameter and of the control constant being set is displayed, along with the value of the constant as set, on alphanumeric display 11.

Figure 3:
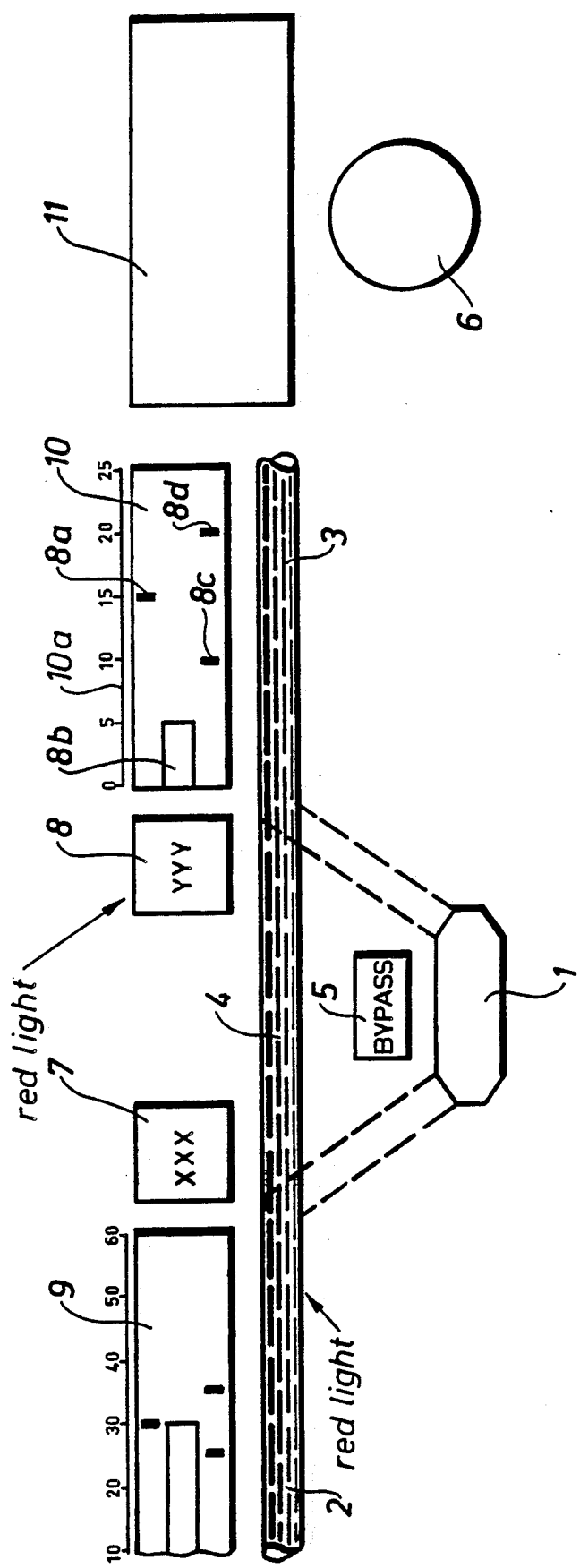

FIG. 3 illustrates the appearance of the front panel when parameter yyy falls outside the upper and lower limits associated with that parameter, and the control microprocessor adjusts the system to bypass the dialyzer. The bar graph 8b reflecting the actual measured value of parameter yyy shows the out-of-limit value. Thus, the right hand edge of the bar graph is at a low level on the scale 10a and is outside the range encompassed by indicia 8a and 8d, corresponding to the lower and upper limits, respectively. To provide a conspicuous alarm signal indicating that parameter yyy is outside of the limits, supervisory microprocessor 44 (FIG. 6) causes illuminator 60 to illuminate actuator 8 with a red light. At the same time, the supervisory microprocessor illuminates bypass alarm indicator 5.

The supervisory microprocessor also adjusts pictorial illumination means 56 to illuminate the pictorial representation 2 of the inlet conduit, the pictorial representation 4 of the bypass conduit, and the pictorial representation 3 of the outlet conduit with a red light. The pictorial representations 2a and 3a of the branch conduits leading to and from the dialyzer are left unilluminated. These pictorial representations thus instantly inform the operator that the system is in a bypass condition. The red color of the illuminated representation provides a further signal that the bypass condition is the result of an abnormal, out-of-limit condition. These signals are supplemented by the bypass alarm light 5. The alarm indication provided by illuminated actuator 8 guides the operator to instant identification of the particular parameter which is out-of-limits, and which has caused the abnormal condition. Because all of the actual values and control constants for the various parameters are continually displayed on the associated graphic displays, the operator can promptly diagnose the nature of the malfunction.

Figure 4:
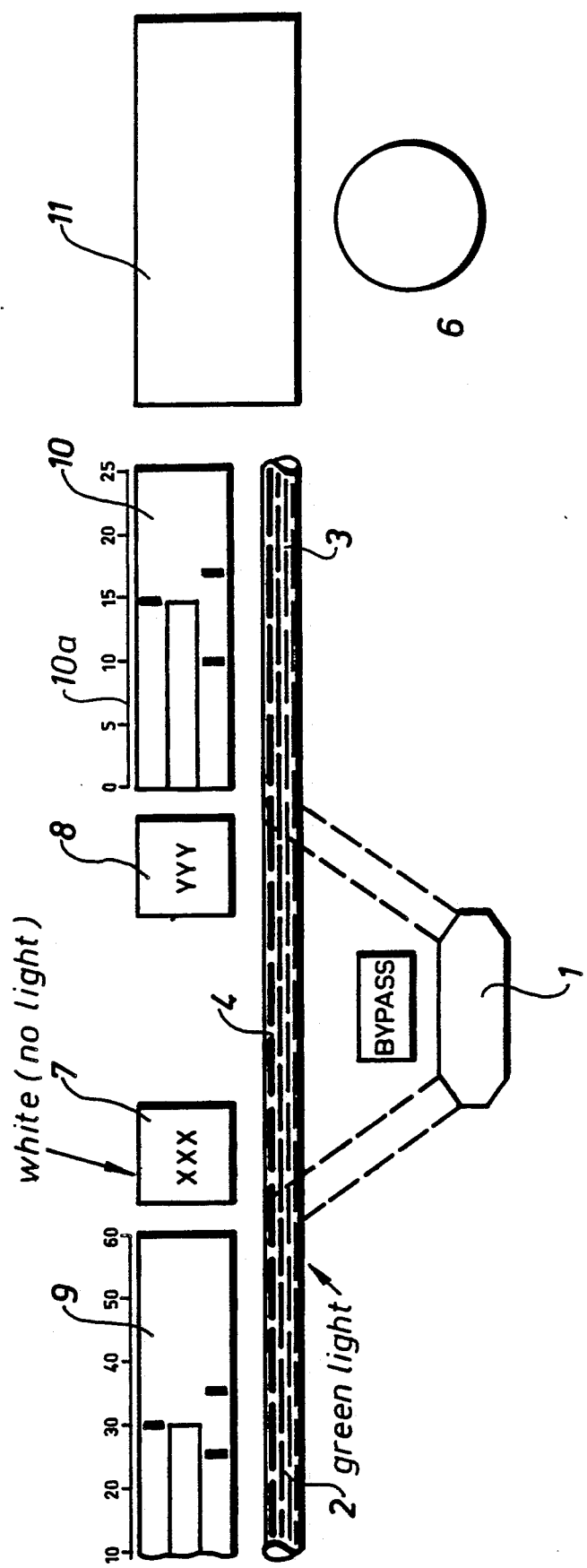

As is illustrated in FIG. 4, the system may be deliberately switched into a bypass mode, for example as part of a predetermined schedule of operations, and this can be done even where none of the parameters is in an out-of-limit condition. In this case, the illuminators associated with actuators 7 and 8 are left unilluminated, so that no alarm signal is given. Also, although the pictorial representation means is adjusted by the supervisory microprocessor to illuminate pictorial representations 2, 3 and 4 to show the bypass flow, and to leave representations 2a and 3a unilluminated to show that no flow is going through the dialyzer, the pictorial representation is illuminated in green light, rather than red light. Thus, whether or not there is an alarm condition, the pictorial representation can be employed to show the actual flow path in use within the system.

Figure 5:
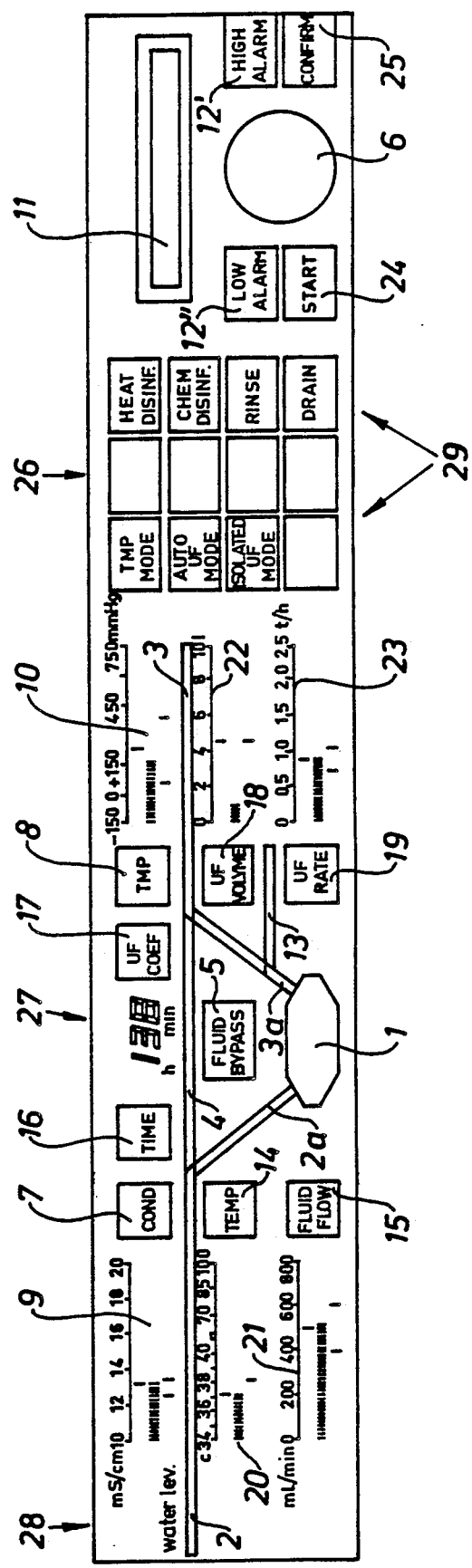
FIG. 5 is a view similar to FIG. 1 but depicting a larger panel according to the present invention for control of a plurality of different parameters in a dialysis system.

Typically, the systems controlled by the apparatus in accordance with the present invention require control of more than two parameters as is employed in the systems of FIGS. 1-4 and 6. FIG. 5 thus depicts the front face of a control panel, as can be used in controlling dialysis fluid flow in a hemodialysis system. The panel of FIG. 5 incorporates the same elements as mentioned above in connection with FIGS. 1-4 and 6. Elements common to both embodiments are denoted in FIG. 5 by the same reference numerals as those employed in FIGS. 1-4 and 6. However, display 9 is associated in FIG. 5 with the real parameter of fluid conductivity, and the associated adjacent actuator 7 is marked with the legend "COND", rather than with the nominal legend appearing on the corresponding actuator appearing in FIG. 2. Likewise, the graphic display 10 is associated with the real parameter transmembrane pressure, and the associated adjacent actuator 8 is marked with the legend "TMP", rather than with the nominal legend "yyy," as in the other figures. The pictorial representation on the front face of the panel in FIG. 5 includes the same elements as the pictorial representation of FIGS. 1-4 but also includes a pictorial representation 13 of an additional branch conduit carrying an ultrafiltrate flow. Additional graphic representations 22 and 23 associated with ultrafiltrate volume and ultrafiltration rate parameters, both of which pertain to the flow in the ultrafiltrate conduit represented by branch 13, are disposed on the panel front face adjacent this branch of the pictorial representation. Actuators 18 and 19 which are associated, respectively, with ultrafiltrate volume and ultrafiltration rate, are disposed adjacent to graphic displays 22 and 23, respectively. Furthermore, additional graphic displays 20 and 21 for incoming dialysis fluid temperature in the inlet represented by pictorial representation 2, and fluid flow in the inlet 2, respectively, are disposed adjacent to the pictorial representation of the inlet conduit. Actuators 14 and 15 relating to these parameters are disposed adjacent to these additional displays. The panel of FIG. 5 incorporates additional buttons 26 for setting the system to operate in different modes. Thus, each of these buttons may be linked to the control and supervisory microprocessors of the system, so that these microprocessors, and hence the system as a whole, can operate according to different programs, depending upon which of the buttons is actuated. For example, depression of the button 26 marked "TMP Mode" sets the system to operate so as to maintain the transmembrane pressure constant, whereas operation of the button 26 marked "Auto UF Mode" sets the system to perform a dialysis procedure with accurately controlled ultrafiltration. Operation of the button marked "Isolated UF Mode" sets the system to perform a pure ultrafiltration procedure without any dialysis fluid flow. Likewise, the buttons marked "HEAT DISNF", "CHEM DISNF", "RINSE" and "DRAIN" sets the system to perform the corresponding heat sterilization, chemical sterilization, rinsing or emptying of functions The panel of FIG. 5 also includes a clock display 27. This clock display is associated with and adjacent to an actuator 16 marked "TIME". Operation of this actuator combined with adjustment of the knob or maneuvering element 6 sets the time in internal clocks within the microprocessors of the system. The panel of FIG. 5 also includes additional displays for showing information other than the values and control constants for the parameters set from the panel. Thus, digital display 28 marked "WATER LEV" indicates the fluid level in a vessel for containing dialysis fluid. The panel of FIG. 5 also includes a start button 24 and a button 25 marked "CONFIRM" disposed adjacent maneuvering element or knob 6.

Operation of the panel shown in FIG. 5 is substantially the same as operation of the panel described above with reference to FIGS. 1-4 and 6. Thus, to set the upper limit for transmembrane pressure, the operator actuates actuator 8 adjacent display 10 for transmembrane pressure, and also actuates the high limit button 12' adjacent to maneuvering element or knob 6. The variable signal produced upon actuation of this element is interpreted as a new value for the transmembrane pressure upper limit, which is displayed on alphanumeric display 11. However, in operation of the panel according to FIG. 5, the control system does not begin to apply the new value so set until the operator signals that he is satisfied with the new value displayed on display 11 by pressing CONFIRM button 25. To permit this function, each of the storage registers associated with the microprocessors may be provided with a temporary storage location, distinct from the storage locations for the parameters actually in use, and each microprocessor may be arranged to shift the newly set value from the temporary storage location to the storage location assigned to the parameter when the CONFIRM button is depressed.

Numerous variations and combinations of the features described above can be employed in accordance with the present invention. Thus, in one variant of the invention, the upper and lower limits are not set directly. Instead, the system is arranged to calculate upper and lower limits for each parameter from the set point selected by the operator for such parameter. The upper and lower limits may be calculated from the set point according to a predetermined formula or algorithm. In this case, the control constant selection means may be omitted and the high limit and low limit selector buttons 12' and 12" may likewise be omitted. Also, the layout of the fluid flow path and the control panel face may make it impossible to dispose each graphic display and the associated actuator immediately adjacent the pictorial representation of the pertinent portion of the fluid flow path. Thus, some of the graphic displays may be disposed adjacent related pictorial representations, whereas other graphic displays may be disposed at more remote locations. In less preferred embodiments, the pictorial representation may be omitted entirely, and the graphic displays may be replaced by other forms of display. In another less preferred embodiment, alphanumeric display 11 may be omitted entirely, and the supervisory microprocessor may be arranged to display the new value set for each control constant only on the related graphic display.

As will be readily appreciated, the layout of the panel face, and the particular parameters and actual constants employed, will vary with the nature of the system to be controlled.

Typically, in control of the dialysis fluid portion of a hemodialysis system, the control panel should be arranged to set control constants for one or more of the following functions: conductivity, temperature, fluid flow, transmembrane pressure, ultrafiltrate volume, ultrafiltration rate, time, chemical composition, pH and blood leakage monitoring. In control of the blood-handling portion of a hemodialysis system, control constants for one or more of the following parameters should be set by use of a control panel in accordance with the present invention: temperature, blood flow, transmembrane pressure, venous pressure, arterial pressure, chemical composition and the presence of air. In a particularly preferred arrangement, the control panel according to the present invention is configured to control both blood handling portion and the hemodialysis fluid flow portion of the system. A control panel for such use would typically incorporate pictorial representations of the flow paths for both blood and dialysis fluid. As the present invention provides important improvements in monitoring and control of operating parameters in hemodialysis fluid flow and/or blood flow in hemodialysis operations, the invention provides improved methods of controlling these functions. In the improved methods control panels and systems in accordance with the present invention are employed and operated as described above.

In the embodiments described above, particularly with reference to FIG. 6, the digital duplication means takes the new value for each control parameter, duplicates it and enters the new value into the storage registers associated with both the supervisory and the control microprocessor. However, in a variant to this approach, a "dummy" storage register is provided which is not operatively associated with either of the microprocessors. The input means may be arranged to direct new values into the dummy storage register and the digital duplication means may be arranged to copy the values from the dummy storage register into the storage registers associated with the supervisory and control microprocessors. In the apparatus described above, the comparison and substitution means checks the new value for every control constant. However, the apparatus can be arranged so that the less significant or noncritical control constants are not so checked.

As these and other variations and combinations of the features described above may be employed, the foregoing descriptions of the embodiments should be taken as illustrating, rather than as limiting, the present invention as defined by the claims.

What is claimed is:

1. A control panel for use with a system having means for regulating a plurality of parameters according to at least one control constant associated with each parameter, said control panel comprising:
   (a) a plurality of separate display means, one of said display means being associated with each of said parameters, each of said display means being operative to display the value of a control constant employed by said system for the associated parameter;
   (b) variable signal means including a single manually-movable maneuvering element for providing a manually variable signal dependent upon the position of said maneuvering element;
   (c) parameter selection means including a plurality of manually operably actuators, one of said actuators being associated with each of said display means and disposed on said control panel adjacent thereto on said panel for selecting the parameter associated with each of said display means upon operation of said manually operable actuator associated therewith; and
   (d) interpretation means for interpreting said variable signal provided by said variable signal means as a new value of said control constant for the parameter selected by said parameter selection means and supplying said new value to said system.

2. The control panel of claim 1 further comprising indicator means for altering the appearance of said display means associated with the parameter selected by said manually operable actuator.

3. The control panel of claim 2 wherein each of said display means includes at least one illuminated element and said indicator means includes means for flashing said at least one illuminated element of said display means associated with the parameter selected by said manually operable parameter selection means.

4. The control panel of claim 1 for use with a system arranged to regulate each of said parameters according to a plurality of different control constants, said control panel further comprising manually operable control constant selector means for selecting a particular one of said plurality of control constants for the parameter selected by said parameter selection means, said interpretation means being operative to interpret said variable signal as a new value of the particular control constant selected by said parameter selector means for the parameter selected by said parameter selection means.

5. The control panel of claim 4, wherein said plurality of different control constants for each of said parameters includes a set point, a lower limit and an upper limit.

6. The control panel of claim 5, wherein said control constant selector means includes default means for automatically selecting said set point, and means for selecting said upper limit or said lower limit only upon manual actuation of said control constant selector means.

7. In a method of controlling the blood portion of hemodialysis, the improvement comprising the step of setting control constant values for controlling at least one parameter selected from the group consisting of temperature, blood flow, transmembrane pressure, venous pressure, arterial pressure, chemical composition, and air inclusion using the control panel of claim 5.

8. The control panel of claim 1, for use with a system arranged to regulate each of said parameters according to a set point, an upper limit and a lower limit, said interpretation means being operative to interpret said variable signal as a new value for said set point of the parameter selected by said parameter selection means, said control panel further comprising limit adjustment means for automatically determining new values of said upper and lower limits for the parameter selected by said parameter selection means in accordance with a predetermined relationship to the new value of said set point for the selected parameter, and for supplying said new values of said upper and lower limits to said system.

9. The control panel of claim 1 wherein each of said display means includes measured value display means for displaying the actual measured value of the associated parameter.

10. A control panel of claim 9 wherein each of said display means includes graphic means for representing the actual value of the associated parameter and the value of each control constant for the associated parameter as locations along a common scale.

11. The control panel of claim 10 further comprising alphanumeric display means for displaying information representative of the identity of the parameter selected by said parameter selection means 12. The control panel of claim 11 wherein said alphanumeric display means further includes data display means for displaying data representing the new value of said control constants supplied to the system.

13. The control panel of claim 1 for use with a system incorporating at least one fluid flow path, at least one of said parameters pertaining to a condition prevailing at a predetermined location in said fluid flow path, said control panel further comprising a pictorial representation of said fluid flow path, said display means associated with said at least one of said parameters being disposed along said pictorial representation in positions corresponding to the locations on said fluid flow path to which the associated parameters pertain.

14. The control panel of claim 13, for use with a system including a plurality of alternate flow paths, said pictorial representations including a plurality of alternate displays representative of said alternate flow paths, further comprising means for selectively illuminating the alternate representation corresponding to the particular flow path in use in said system.

15. In a method of controlling the dialysis fluid portion of a hemodialysis system, the improvement comprising the step of setting control constant values for at least one parameter selected from the group consisting of conductivity, temperature, fluid flow, transmembrane pressure, ultrafiltrate volume, ultrafiltration rate, time, chemical composition, ph, and blood leakage using the control panel of claim 1.

16. Control apparatus comprising:
   (a) a plurality of microprocessors;

(b) a plurality of storage registers, the number of storage registers being at least equal to the number of said microprocessors, one of said storage registers being associated with each of said microprocessors, each of said microprocessors being arranged to control and/or monitor the same common parameters, each of said microprocessors applying values of control constants stored in the associated storage register in monitoring and/or controlling said parameters;

(c) manually controllable input means for supplying new values of said control constants;

(d) digital duplication means for digitally duplicating the new values of the said control constants supplied by said input means and entering said duplicated values into all of said storage registers, whereby identical values for said control constants are entered into all of said storage registers; and (e) display means for displaying said new values of said control constants as entered into at least one of said storage registers.

17. Control apparatus of claim 16 wherein said digital duplication means is operative to enter said new values into one of said storage registers which is associated with one of said microprocessors, and to copy said new value from said one of said storage registers into each other one of said storage registers, and wherein said display means is operative to display the values entered in a storage register associated with another one of said microprocessors.

18. The control apparatus of claim 17 wherein one of said microprocessors is a control microprocessor arranged to regulate the values of said parameters based upon a comparison of measured values for said parameters with the values of said control constants stored in said storage register associated with said control microprocessor, and wherein another one of said microprocessors is a supervisory microprocessor arranged to generate an alarm signal based upon a comparison of measured values for said parameters with the values of control constants stored in said storage register associated with said supervisory microprocessor.

19. The apparatus of claim 18 wherein said display means is operative to display said new values entered in said storage register associated with said supervisory microprocessor.

20. The apparatus of claim 16 wherein said digital duplication means is incorporated into one of said microprocessors.

* * * * *

UNITED STATES PATENT AND TRADEMARK OFFICE
CERTIFICATE OF CORRECTION

PATENT NO. : 4,990,258

DATED : February 5, 1991

INVENTOR(S) : Bjare et al.

It is certified that error appears in the above-identified patent and that said Letters Patent is hereby corrected as shown below:

Column 6, line 51, "par-meter" should read --parameter--.

Column 9, line 26, "12" should read --12'--.

Column 10, line 54, after "legend" insert --"xxx"--.

Signed and Sealed this

Eleventh Day of August, 1992

Attest:

DOUGLAS B. COMER

*Attesting Officer*     Acting Commissioner of Patents and Trademarks